United States Patent [19]

Kim

[11] Patent Number: 5,767,274

[45] Date of Patent: Jun. 16, 1998

[54] PRENYL TRANSFERASE INHIBITORS

[75] Inventor: Sun H. Kim, Needham, Mass.

[73] Assignee: Biomeasure, Incorporated, Milford, Mass.

[21] Appl. No.: 675,439

[22] Filed: Jun. 28, 1996

[51] Int. Cl.⁶ .................... C07D 285/38; A61K 31/385
[52] U.S. Cl. ............................ 540/467; 514/183
[58] Field of Search .................................. 540/467

[56] References Cited

U.S. PATENT DOCUMENTS

| | | | |
|---|---|---|---|
| 5,439,918 | 8/1995 | deSolms et al. | 514/307 |
| 5,491,164 | 2/1996 | deSolms et al. | 514/423 |

FOREIGN PATENT DOCUMENTS

| | | |
|---|---|---|
| 0 618 221 A2 | 10/1994 | European Pat. Off. . |
| 0 696 593 A2 | 2/1996 | European Pat. Off. . |

OTHER PUBLICATIONS

Qian et al., "Design and Synthesis of Non–Peptide Ras CAAX Mimetics as Potent Farnesyltransferase Inhibitors" J. Med. Chem. 39:217–223, 1996.

Reiss et al., "Sequence Requirement for Peptide Recognition by Rat Brain p21$^{ras}$ Protein Farnesyltransferase", Proc. Natl. Acad. Sci. USA 88:732–736, 1991.

Sepp–Lorenzino et al., "A Peptidomimetic Inhibitor of Farnesyl:Protein Transferase Blocks the Anchorage–Dependent and –Independent Growth of Human Tumor Cell Lines", Cancer Research 55:5302–5309, 1995.

Shigematsu et al., "FR901228, A Novel Antitumor Bicyclic Depsipeptide Produced by *Chromobacterium Violaceum* No. 968 II. Structure Determination", The Journal of Antibiotics 47:311–314, 1994.

Singh et al., "Fusidienol: A Novel Inhibitor of Ras Farnesyl–Protein Transferase from Fusidium Griseum", Tetrahedron Letters 35:4693–4696, 1994.

Sugawara et al., "Structure of Malformin A$_2$, Reinvestigation of Phytotoxic Metabolites Produced by *Aspergillus Niger*", Tetrahedron Letters 31:4337–4340, 1990.

Ueda et al., "FR901228, A Novem Antitumor Bicyclic Depsipeptide Produced by *Chromobacterium Violaceum* No. 968 I. Taxonomy, Fermentation, Isolation . . . " The Journal of Antibiotics 47:301–310, 1994.

Ueda et al., "FR901228, A Novel Antitumor Bicyclic Depsipeptide Produced by *Chromobacterium Violaceum* No. 968 III. Antitumor Activities on Experimental Tumors in Mice", The Journal of Antibiotics 47:315–323, 1994.

Vogt et al., "A Non–Peptide Mimetic of Ras–CAAX: Selective Inhibition of Farnesyltransferase and Ras Processing", The Journal of Biological Chemistry 270:660–664, 1995.

Williams et al., "2–Substituted Piperazines as Constrained Amino Acids. Application to the Synthesis of Potent, Non Carboxylic Acid Inhibitors of Farnesyltransferase", J. of Medicinal Chemistry 39:1345–1348, 1996.

Byk et al., "Local Constrained Shifty Pseudopeptides Inhibitors of Ras–Farnesyl Transferase", Bioorganic & Medicinal Chemistry Letters 5:2677–2682, 1995.

Koblan et al., "NMR Studies of Novel Inhibitors Bound to Farnesyl–Protein Transferase", Protein Science 4:681–688, 1995.

Kohl et al., "Development of Inhibitors of Protein Farnesylation as Potential Chemotherapeutic Agents", Journal of Cellular Biochemistry 22:145–150, 1995.

Kohl et al., "Inhibition of Farnesyltransferase Induces Regression of Mammary and Salivary Carcinomas in Ras Transgenic Mice", Nature Medicine 1:792–797, 1995.

Kohl et al., "Selective Inhibition of ras–Dependent Transformation by a Farnesyltransferase Inhibitor", Science 260:1934–1937, Jun. 25, 1993.

Leftheris et al., "Development of Highly Potent Inhibitors of Ras Farnesyltransferase Possessing Cellular and in Vivo Activity", J. Med. Chem. 39:224–236, 1996.

Nigam et al., "Potent Inhibition of Human Tumor p21$^{ras}$ Farnesyltransferase by A$_1$A$_2$–lacking p21$^{ras}$. . . ", The Journal of Biological Chemistry 268:20695–20698, 1993.

Patel et al., "Phenol Based Tripeptide Inhibitors of Ras Farnesyl Protein Transferase", Bioorganic & Medicinal Chemistry Letters 4:1883–1888, 1994.

Qian et al., "Design and Structural Requirements of Potent Peptidomimetic Inhibitors of p21$^{ras}$ Farnesyltransferase", The Journal of Biological Chemistry 269:12410–12413, 1994.

Bishop et al., "Novel Tricyclic Inhibitors of Farnesyl Protein Transferase", The Journal of Biological Chemistry 270:30611–30618, 1995.

Bhide et al., "Rational Design of Potent Carboxylic Acid Based Bisubstrate Inhibitors of Ras Farnesyl Protein Transferase" Bioorganic & Medicinal Chemistry Letters 4:2107–2112, 1994.

Buss et al., "Farnesyl Transferase Inhibitors: The Successes and Surprises of a New Class of Potential Cancer Chemotherapeutics", Chemistry & Biology 2:787–791, Dec. 1995.

deSolms et al., "Pseudodipeptide Inhibitors of Protein Farnesyltransferase", J. Med. Chem. 38:3967–3971, 1995.

(List continued on next page.)

*Primary Examiner*—C. Warren Ivy
*Assistant Examiner*—Charanjit S. Aulakh
*Attorney, Agent, or Firm*—Fish & Richardson; William McGowan; John D. Conway

[57] ABSTRACT

A family of compounds capable of inhibiting the activity of prenyl transferases. The compounds are covered by either of the two following formulas

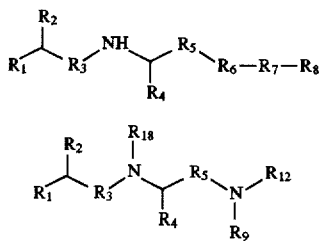

Each of the R groups is defined in the disclosure.

14 Claims, No Drawings

OTHER PUBLICATIONS

Clerc et al., "Constrained Analogs of KCVFM With Improved Inhibitory Properties Against Farnesyl Transferase" Bioorganic & Medicinal Chemistry Letters 16:1779–1784, 1995.

Garcia et al., "Peptidomimetic Inhibitors of Ras Farnesylation and Function in Whole Cells", The Journal of Biological Chemistry 268:18415–18418, 1993.

Graham et al., "Pseudopeptide Inhibitors of Ras Farnesyl–Protein Transferase", J. Med. Chem. 37:725–732, 1994.

Gibbs et al., "Farnesyltransferase Inhibitor: Ras Research Yields a Potential Cancer Therapeutic", Cell 77:175–178, Apr. 22, 1994.

Harrington et al., "Cysteine and Methionine Linked by Carbon Pseudopeptides Inhibit Farnesyl Transferase", Bioorganic & Medicinal Chemistry Letters 4:2775–2780, 1994.

Hunt et al., "Potent, Cell Active, Non-Thiol Tetrapeptide Inhibitors of Farnesyltransferase", J. Med. Chem. 39:353–358, 1996.

James et al., "Benzodiazepine Peptidomimetics: Potent Inhibitors of Ras Farnesylation in Animal Cells", Science 260:1937–1942, Jun. 25, 1993.

James et al., "Polylsine and CVIM Sequences of K–RasB Dictate of Prenylation and Confer Resistance to Benzodiazepine Peptidomimetic in Vitro", The Journal of Biological Chem. 270:6221–6226, 1995.

PRENYL TRANSFERASE INHIBITORS

BACKGROUND OF THE INVENTION

The Ras family of proteins are important in the signal transduction pathway modulating cell growth. The protein is produced in the ribosome, released into the cytosol, and post-translationally modified. The first step in the series of post-translational modifications is the alkylation of Cys[168] with farnesyl or geranylgeranyl pyrophosphate in a reaction catalyzed by prenyl transferase enzymes such as farnesyl tranferase and geranylgeranyl transferase (Hancock, J. F., et al., Cell 57:1167–1177 (1989)). Subsequently, the three C-terminal amino acids are cleaved (Gutierrez, L., et al., EMBO J. 8:1093–1098 (1989)), and the terminal Cys is converted to a methyl ester (Clark, S., et al., Proc. Nat'l Acad. Sci. (USA) 85:4643–4647 (1988)). Some forms of Ras are also reversibly palmitoylated on cysteine residues immediately N-terminal to Cys168 (Buss, J. E., et al., Mol. Cell. Biol. 6:116–122 (1986)). It is believed that these modifications increase the hydrophobicity of the C-terminal region of Ras, causing it to localize at the surface of the cell membrane. Localization of Ras to the cell membrane is necessary for signal transduction (Willumsen, B. M., et al., Science 310:583–586 (1984)).

Oncogenic forms of Ras are observed in a relatively large number of cancers including over 50 percent of colon cancers and over 90 percent of pancreatic cancers (Bos, J. L., Cancer Research 49:4682–4689 (1989)). These observations suggest that intervention in the function of Ras mediated signal transduction may be useful in the treatment of cancer.

Previously, it has been shown that the C-terminal tetrapeptide of Ras has the "CAAX" motif (wherein C is cysteine, A is an aliphatic amino acid, and X is any amino acid). Tetrapeptides having this structure have been shown to be inhibitors of prenyl transferases (Reiss, et al., Cell 62:81–88 (1990)). Poor potency of these early farnesyl transferase inhibitors has prompted the search for new inhibitors with more favorable pharmacokinetic behavior (James, G. L., et al., Science 260:1937–1942 (1993); Kohl, N. E., et al., Proc. Nat'l Acad. Sci. USA 91:9141–9145 (1994); deSolms, S. J., et al., J. Med. Chem. 38:3967–3971 (1995); Nagasu, T. et al., Cancer Research 55:5310–5314 (1995); Lerner, E. C., et al., J. Biol. Chem. 270:26802–26806 (1995); Lerner, E. C., et al., J. Biol. Chem. 270:26770 (1995); and James, et al., Proc. Natl. Acad. Sci. USA 93:4454 (1996)).

Recently, it has been shown that a prenyl transferase inhibitor can block growth of Ras-dependent tumors in nude mice (Kohl, N. E., et al., Proc. Nat'l Acad. Sci. USA 91:9141–9145 (1994)). In addition, it has been shown that over 70 percent of a large sampling of tumor cell lines are inhibited by prenyl transferase inhibitors with selectivity over non-transformed epithelial cells (Sepp-Lorenzino, I. et al., Cancer Research, 55:5302–5309 (1995)).

SUMMARY OF THE INVENTION

In one aspect, the invention features a compound of formula I or formula II

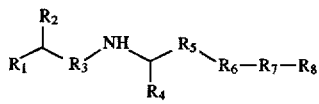

Formula I

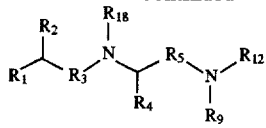

Formula II wherein $R_1$ is $N(R_{10})(R_{11})$;

$R_2$ is thio lower alkyl;

each of $R_3$ and $R_5$, independently, is $CH_2$ or $C(O)$;

$R_4$ is substituted or unsubstituted thio lower alkyl, wherein said substituent is $CH_2NHC(O)R_{13}$ and said substituent is attached to said thio group;

$R_6$ is a residue of a natural or synthetic α-amino acid;

$R_7$ is a residue of a natural or synthetic α-amino acid;

$R_8$ is OH or lower alkoxy, or, together with $R_7$, forms homoserinelactone;

each of $R_9$, $R_{10}$ and $R_{11}$, independently, is H or lower alkyl;

$R_{12}$ is substituted or unsubstituted cycloalkyl, cycloalkyl lower alkyl, aryl, aryl lower alkyl, heterocycle, or heterocycle lower alkyl, wherein said substituent is lower alkyl, aryl, halo, lower alkoxy, or $C(O)$—$R_7$—$R_8$;

$R_{13}$ is lower alkyl, aryl, or aryl lower alkyl; $R_{18}$ is H or, together with $R_9$, forms $CH_2CH_2$; provided if $R_4$ is unsubstituted thio lower alkyl, the free thio group of $R_2$ and the free thio group of $R_4$ may form a disulfide bond; or a pharmaceutically acceptable salt thereof.

In one embodiment, the compound is of formula I where $R_6$ is —$N(R_{14})CH(R_{15})C(O)$— where $R_{14}$ is H or lower alkyl, and $R_{15}$ is substituted or unsubstituted lower alkyl, aryl, aryl lower alkyl, heterocycle, or heterocycle lower alkyl where said substituent is lower alkyl, halo, or lower alkoxy, or where $R_{15}$, together with $NR_{14}C$ attached thereto, form heterocycle; and $R_7$ is —$N(R_{16})CH(R_{17})C(O)$— where $R_{16}$ is H or lower alkyl, and $R_{17}$ is $(CH_2)_mS(O)_nCH_3$ or substituted or unsubstituted lower alkyl, thio lower alkyl, where said substituent is $C(O)N(R_{10})(R_{11})$, m is 1–6, n is 0–2, and $R_8$ is OH or lower alkoxy. In this embodiment, $R_2$ can be $CH_2SH$; $R_4$ can be $C(CH_3)_2SH$ or $CH_2SH$ wherein the free thio group of $R_2$ and the free thio group of $R_4$ form a disulfide bond; $R_{15}$, together with $NR_{14}C$ attached thereto, can form heterocycle; $R_{16}$ can be H; and $R_{17}$ can be $(CH_2)_2S(O)_nCH_3$; furthermore, $R_1$ can be NH2; $R_3$ can be $CH_2$; $R_5$ can be CO; and $R_8$ can be OH or $OCH_3$. In the same embodiment, $R_2$ can be $(CH_2)SH$; $R_4$ can be $C(CH_2)_2SCH_2NHCOCH_3$ or $CH_2SCH_2NHCOCH_3$; $R_{15}$, together with $NR_{14}C$ attached thereto, can form heterocycle; $R_{16}$ can be H, and $R_{17}$ can be $(CH_2)_2S(O)_nCH_3$; furthermore, $R_1$ is NH2; $R_3$ is $CH_2$; $R_5$ is $C(O)$; and $R_8$ is OH or $OCH_3$.

In another embodiment, the compound is of formula II, wherein $R_2$ is $CH_2SH$; $R_4$ is $C(CH_3)_2SH$ or $CH_2SH$ wherein the free thio group of $R_2$ and the free thio group of $R_4$ form a disulfide bond; $R_{12}$ is substituted or unsubstituted aryl or aryl lower alkyl, and $R_{18}$ is H. In this embodiment, $R_1$ can be NH2; $R_3$ can be $CH_2$; $R_5$ can be $C(O)$; $R_9$ can be H; and $R_{12}$ can be substituted or unsubstituted phenyl or benzyl, wherein said substituent is lower alkyl or halo.

In a still further embodiment, $R_2$ is $(CH_2)SH$; $R_4$ is $C(CH_2)_2SCH_2NHCOCH_3$ or $CH_2SCH_2NHCOCH_3$; and $R_{12}$ is substituted or unsubstituted aryl or aryl lower alkyl. In this embodiment, $R_1$ can be NH2; $R_3$ can be $CH_2$; $R_5$ can be CO; $R_9$ can be H; and $R_{12}$ can be substituted or unsubstituted phenyl or benzyl, wherein said substituent is lower alkyl or halo.

Examples of the present invention include the following:
Compound 1
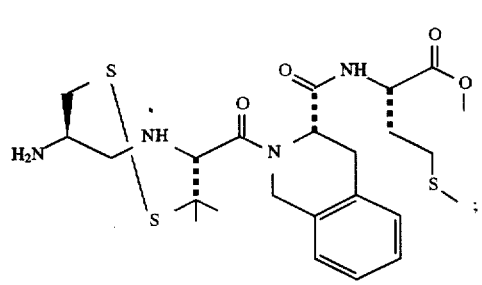
Compound 2
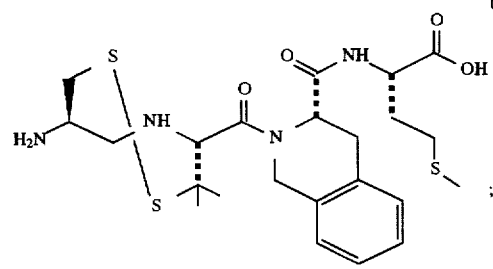
Compound 3
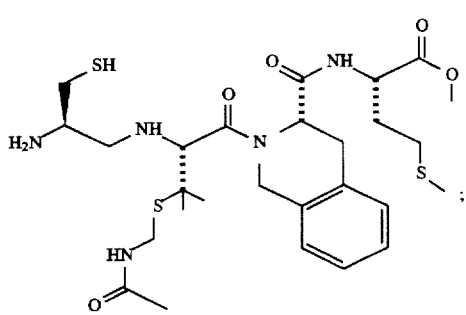
Compound 4
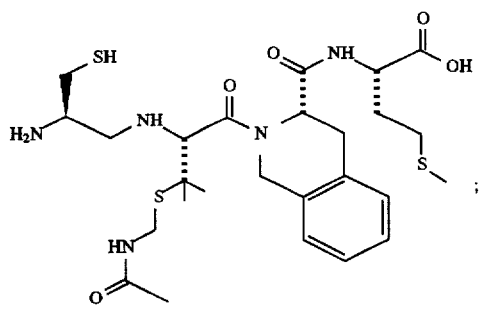
Compound 5
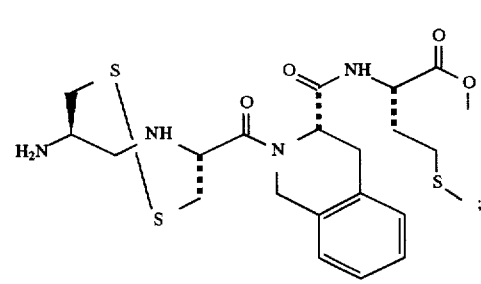
Compound 6
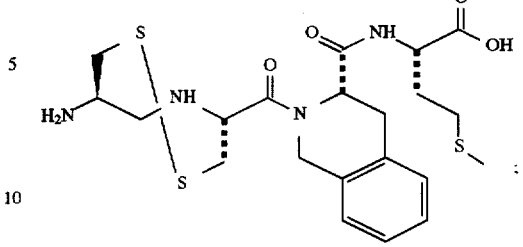
Compound 7
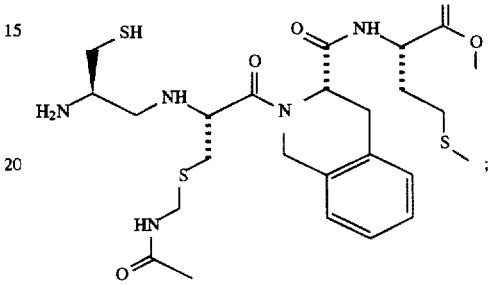
Compound 8
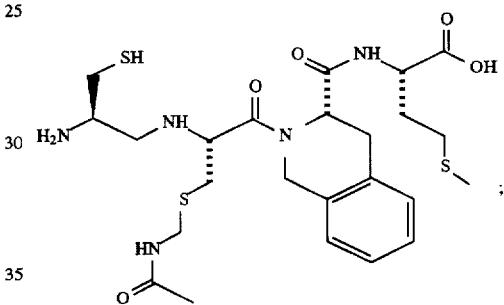
Compound 9
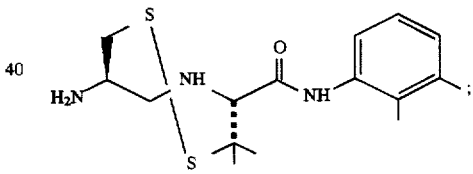
Compound 10
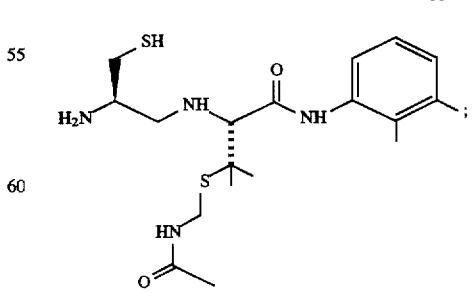
Compound 11
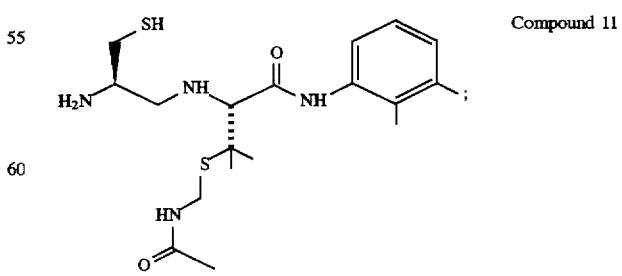

Compound 12
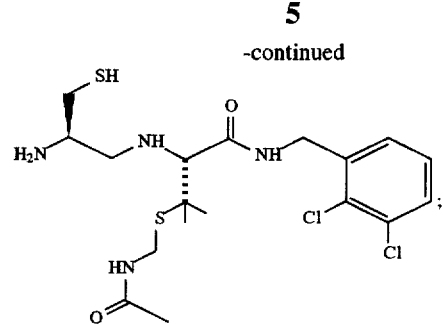
Compound 18
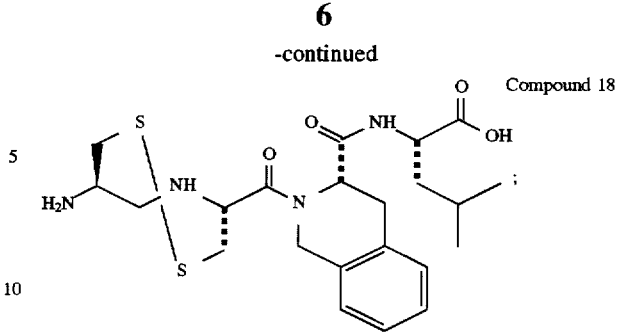
Compound 13
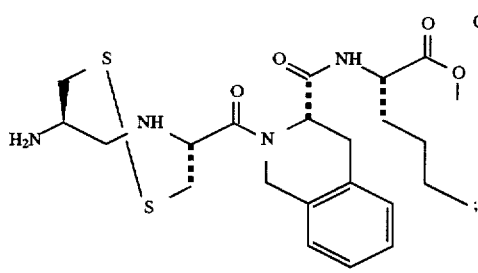
Compound 19
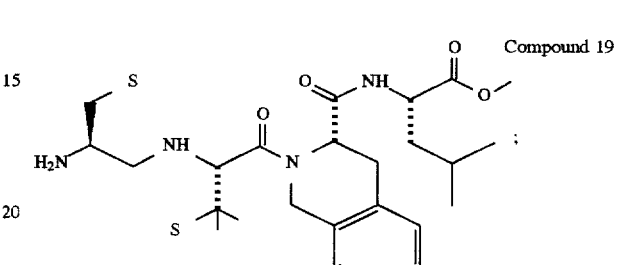
Compound 14
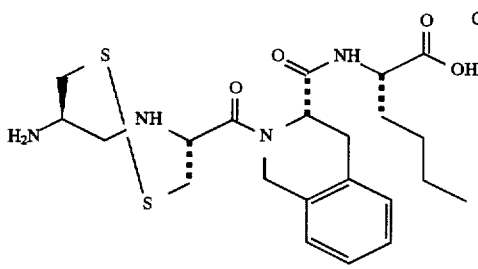
Compound 20
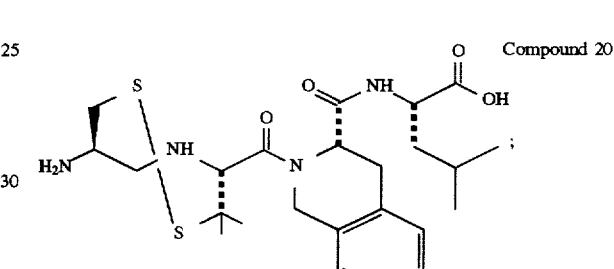
Compound 15
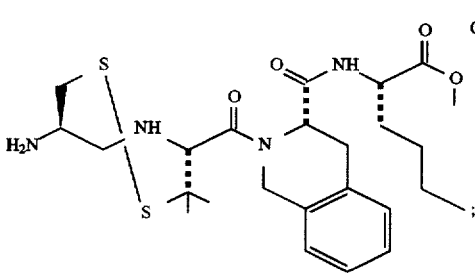
Compound 21
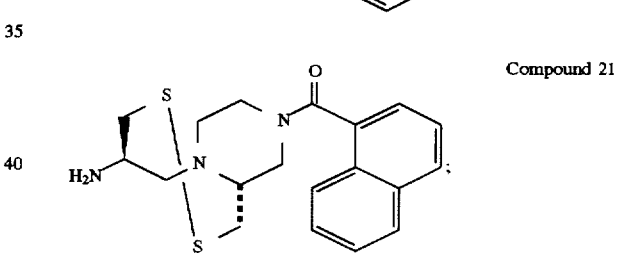
Compound 16
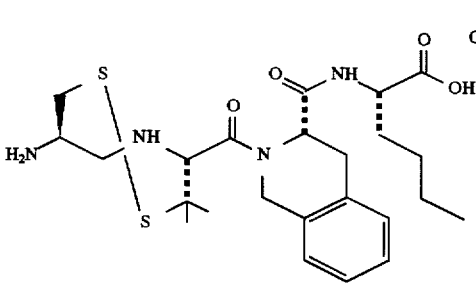
Compound 22
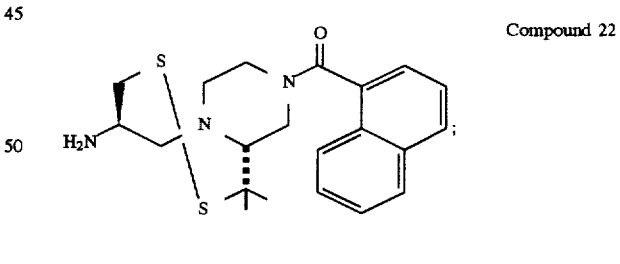
Compound 17
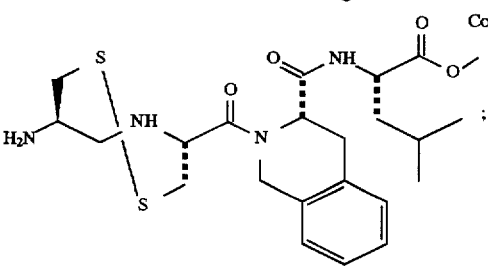
Compound 23
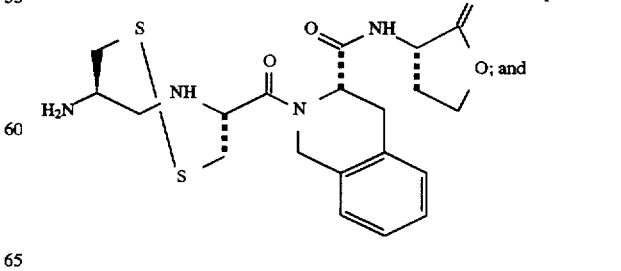
O; and -continued

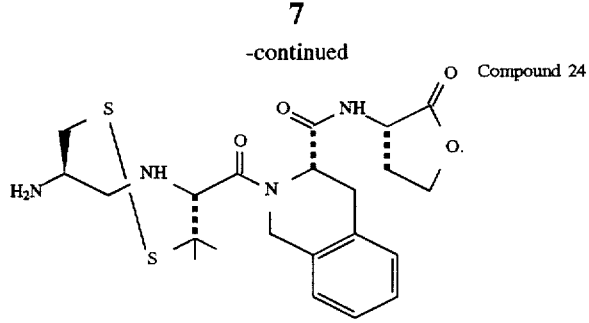

Compound 24

The compounds of the present invention may have asymmetric centers and occur as racemates, racemic mixtures, and as individual diastereomers, with all possible isomers, including optical isomers, being included in the present invention. For simplicity, where no specific configuration is depicted in the structural formulae, it is understood that all enantiometric forms and mixtures thereof are represented.

As used herein, "lower alkyl" is intended to include saturated aliphatic hydrocarbon groups having 1–6 carbon atoms. Examples of lower alkyl groups include methyl, ethyl, propyl, isopropyl, butyl, isobutyl, sec-butyl, t-butyl, and the like. "Lower alkoxy" groups include those groups having 1–6 carbons. Examples of lower alkoxy groups include methoxy, ethoxy, propoxy, isopropoxy, and the like. All alkyl and alkoxy groups may be branched or straight chained, but are noncyclic. The term "cycloalkyl" means a 3–7 carbon ring. Examples of cycloalkyl groups include cyclopropyl, cyclobutyl, cyclopentyl, cyclohexyl, and cycloseptyl. The term "halo" means chloro, bromo, iodo, or fluoro. The terms "heterocycle lower alkyl," "thio lower alkyl," "cycloalkyl lower alkyl", and "aryl lower alkyl," are substituted, respectively, with one to three heterocycle, thio, cycloalkyl, and aryl groups.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term heterocycle, as used herein, represents a stable 5- to 7-membered monocyclic or stable 8- to 11-membered bicyclic or stable 11 to 15-membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thiazolidinyl, thienofuryl, thienothienyl, thienyl, and the like.

When a group is substituted, it may be substituted one to four times. The various substituents may be attached to carbon atoms or to heteroatoms (e.g., S, N, or O).

As used herein, the term "residue of an α-amino acid" stands for an α-amino acid residue which is either a natural α-amino acid which is found in nature (e.g., cysteinyl, methionyl, phenylalaninyl, leucinyl, etc.) or a synthetic α-amino acid which is not found in nature (e.g., neurleucyl or the residue of 1,2,3,4-tetrahydroisoguinoline-3-carboxylic acid or penicillamine, etc.).

The compounds of this invention can be provided in the form of pharmaceutically acceptable salts. Acceptable salts include, but are not limited to acid addition salts of inorganic acids such as acetate, maleate, fumarate, tartrate, succinate, citrate, lactate, methanesulfonate, p-toluenesulfonate, pamoate, salicylate, oxalate, and stearate. Also within the scope of the present invention, where applicable, are salts formed from bases such as sodium or potassium hydroxide. For further examples of pharmaceutically acceptable salts see, "Pharmaceutical Salts," J. Pharm. Sci. 66:1 (1977).

In another aspect, the invention features a method of inhibiting prenyl transferases (e.g., farnesyl transferase or geranylgeranyl transferase) in a subject, e.g., a mammal such as a human, by administering to the subject a therapeutically effective amount of a compound of formula I or formula II. In particular, the present invention also covers a method of treating restenosis or tissue proliferative diseases (i.e., tumor) in a subject by administering to the subject a therapeutically effective amount of a compound or its salt. Examples of a tissue proliferative disease include both those associated with benign (e.g., non-malignant) cell proliferation such as fibrosis, benign prostatic hyperplasia, atherosclerosis, and restenosis, and those associated with malignant cell proliferation, such as cancer (e.g., ras-mutant tumors). Examples of treatable tumors include breast, colon, pancreas, prostate, lung, ovarian, epidermal, and hematopoietic cancers (Sepp-Lorenzino, I, et al., Cancer Research 55:5302 (1995)).

A therapeutically effective amount of a compound of this invention and a pharmaceutically acceptable carrier substance (e.g., magnesium carbonate, lactose, or a phospholipid with which the therapeutic compound can form a micelle) together form a pharmaceutical composition (e.g., a pill, tablet, capsule, or liquid) for administration (e.g., orally, intravenously, transdermally, or subcutaneously) to a subject in need of the compound. The pill, tablet, or capsule can be coated with a substance capable of protecting the composition from the gastric acid or intestinal enzymes in the subject's stomach for a period of time sufficient to allow the composition to pass undigested into the subject's small intestine.

The dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as a "therapeutically effective amount."

Also contemplated within the scope of the invention are a method of preparing the compounds of formula I or formula II and the novel chemical intermediates used in these syntheses as described herein.

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

The following is a description of the synthesis of compounds 1, 4, and 9. Other compounds of the invention can be prepared in an analogous manner by a person of ordinary skill in the art.

The compounds of the invention were prepared using standard solution phase methodologies, e.g., as described in Greenstein, et al., Chemistry of the Amino Acids, Vols. 1–3 (J. Wiley, New York (1961)); and M. Bodanszky, et al., The Practice of Peptide Synthesis (Springer-Verlag, 1984)). The condensation reactions were carried out in an inert organic solvent, e.g., dimethylformide, dichloromethane, tetrahydrofuran, benzene or acetonitrile, using a suitable mild condensing agent, e.g., 1-(3-dimethylaminopropyl)-3-ethylcarbodiimide-HCl (EDC, O-benzotriazol-1-yl-N,N,N',N'-tetramethyluronium hexafluorophosphate (HBTU), and optionally a catalyst, e.g., 1-hydroxybenzotriazole (HOBT). The reaction temperature was maintained below room temperature (−15° C. to room temperature) in order to minimize side reactions. Cyclic disulfide formation was carried out under high dilute condition using iodine in various solvents (e.g., methanol, tetrahydrofuran (THF), acetic acid, water, etc.). B. Kamber, et al., Helv. Chim. Acta, 63(96):899 (1980). The intermediate and final products were isolated and purified by standard methods, e.g., column chromatography or HPLC. Compounds where $R_8$, together with $R_9$, forms $CH_2CH_2$ can be made according to the methods of Williams, et al., J. Med. Chem. 39(7):1346 (1996), e.g., by starting with protected cysteine.

EXAMPLE I

N-[2-(R)-amino-3-mercaptopropyl]-L-penicillaminyl-1, 2,3,4-tetrahydro-3(s)-isoquinoline carbonyl methionine methylester cyclic disulfide
(Compound 1)

a) N-t-butoxycarbonyl-S-trityl-L-cysteinyl-N,O-dimethylamide

To an ice-cooled solution of N-t-butoxycarbonyl-L-cysteine (8.0 g) and N,O-dimethylhydroxylamine hydrochloride (7.1 g) in 80 ml dimethylformide was added 4.2 ml diethylcyanophosphonate and 14.7 ml diisopropylethylamine, and after stirring at 0° C. for 1 hr, the reaction mixture was allowed to room temperature overnight. Volatile substances were removed in vacuo to dryness, and the residue was partitioned between ethylacetate and water. Ethylacetate layer was washed with aqueous $NaHCO_3$, water, and dried ($MgSO_4$). Solvent was evaporated in vacuo to dryness, and the residue was chromatographed on silica gel (165 g) using $CHCl_3$ as an eluant. Appropriate fractions were pooled, and solvent was removed in vacuo to dryness. White foam 8.08 g TLC (silica gel: $CHCl_3$/acetone=9:1 $R_f$=0.58).

b) 2(R)-t-Butoxycarbonylamino-3-triphenylmethylmercapto-propanal

To an ice-cooled solution of N-t-Butoxycarbonyl 8-trityl-L-cysteinyl-N,O-dimethylamide (0.85 g) in 20 ml tetrahydrofuran (THF) was added dropwise 3 ml 1.0 M $LiAH_4$ in THF under nitrogen atmosphere. After the mixture was stirred for 30 min. at 0° C., 1M $KHSO_4$ was slowly added, and the resulting emulsion was filtered through celite pad and further washed with ethylacetate. After drying over anhydrous $MgSO_4$, the solvent was removed in vacuo to dryness resulting in 0.7 g of the above-titled compound TLC (silica gel; $CHCl_3$/acetone=4:1; Rf=0.88).

c) N-t-butoxycarbonyl-S-acetamidomethylpenicillaminyl-1, 2,3,4-tetrahydro-3(S)-isoquinolinecarbonyl-methionine methylester To an ice-cooled solution of N-t-butoxycarbonyl-L-1, 2,3,4-tetrahydro-3(S)-isoquinoline (2.77 g) and L-methionine methylester hydrochloride (2.0 g), 1-hydroxybenzotriazole (HOBT) (1.37 g) and O-Benzotriazol-1-yl-N,N,N',N'-tetramethyluronium hexafluorophosphate (HBTU) (3.87 g) in 30 ml dimethylformide was added 4.9 ml diisopropylethylamine (DIEA). After stirring at 0° C. for 30 min, the reaction mixture was allowed to room temperature overnight. Volatile substances were evaporated in vacuo to dryness, and the residue was partitioned between EtOAc and water. EtOAc layer was washed with aqueous $NaHCO_3$, water, and dried ($MgSO_4$). Solvent was evaporated in vacuo to dryness. It was treated with 50% trifluoracetic acid in chloroform (40 ml) containing 4.8 ml triethylsilane for 1 hour, and volatile substances were removed in vacuo to dryness. Trace of trifluoroacetic acid (TFA) was further evaporated with toluene. To the above L-1,2,3,4-tetrahydro-3(S)-isoquinolinecarbonyl methionine methylester TFA salt (2.2 g) in dichloromethane (20 ml) cooled to 0°C. was added 1.2 ml DIEA followed by a solution of HOBT (0.7 g), N-t-butoxycarbonyl-S-acetamidomethyl penicillin (1.6 g) in DMF (3 ml), and EDC (1.2 g). The mixture was stirred at 0° C. for 30 min and then allowed to room temperature overnight. Volatile substances were removed in vacuo to dryness. The residue was partitioned between EtOAc and water. Ethylacetate layer was washed with aqueous $NaHCO_3$, water, and then dried ($MgSO_4$). Solvent was evaporated in vacuo to dryness to yield 3.3 g orange solid.

d) L-[S-acetamidomethylpenicillaminyl-1,2,3,4-tetrahydro-3[S]-isoquinolinecarbonyl methionine methylester and its TFA salt N-t-butoxycarbonyl-S-acetamidomethyl-penicillaminyl-1,2,3,4-tetrahydro-3[S]-isoquinolinecarbonyl methionine methylester (3.3 g) was treated with 50% TFA in $CH_2Cl_2$ (20 ml) containing 1 ml triethylsilane for 30 min. Volatile substances were removed in vacuo to dryness. Trace of TFA was removed by co-evaporation with toluene several times. The TFA salt was dissolved in $CHCl_3$ (30 ml), treated with excess triethylamine, washed with water, dried ($MgSO_4$), and solvent was evaporated in vacuo to give free base.

e) N-[2(R)-(t-butoxycarbonyl)amino-3-triphenylmethylmercapto-propyl]-L-[S-acetamidomethyl-penicillaminyl]-1, 2,3,4-tetrahydro-3(S)-isoquinolinecarbonyl methionine methylester To a solution of 2(R)-t-butoxycarbonylamino-3-triphenylmethyl-mercapto-propanal (0.7 g) and L-[S-acetamidomethylpenicillaminyl-1, 2,3,4-tetrahydro-3(s)-isoquinolinecarbonyl methionine methylester (0.43 g) in $CH_2Cl_2$ (20 ml) containing 1% acetic acid was added triacetoxysodiumborohydride $Na(OAc)_3BH$ (360 mg) in one portion. After stirring for 2 hours, the mixture was washed with water, 5% aqueous $NaHCO_3$, water, and then dried ($MgSO_4$). The solvent was evaporated in vacuo to dryness, and the residue was chromatographed on silica gel (50 g) using $CHCl_3$/acetone (19:1 to 9:1) as eluants. Appropriate fractions were pooled and solvents were removed in vacuo to dryness resulting in a white foam (390 mg) of the above title compound. TLC (silica gel; $CHCl_3$/acetone=4:1; Rf=0.4).

f) N-[2(R)-(t-butoxycarbonyl)amino-3-mercaptopropyl]-L-penicillaminyl]-1,2,3,4-tetrahydro-3(S)-isoquinoline carbonyl methionine methylester cyclic disulfide To a solution of N-[2(R)-(t-butoxycarbonyl)amino-3-triphenylmethylmercaptopropyl]-L-[S-acetamidomethyl-penicillaminyl]-1,2,3,4-tetrahydro-3(S)-isoquinoline carbonyl methionine methylester (500 mg) in 50 ml 90% aqueous MeOH was added dropwise a solution of iodine (250 mg) in methanol (MeOH) (10 ml). After stirring for 1 hour, most of methanol was removed in vacuo to a small volume, diluted with water, and extracted with ethylacetate. The ethylacetate extract was washed with water, aqueous $Na_2S_2O_3$, water, and then dried ($MgSO_4$). The solvent was evaporated in vacuo to dryness resulting in 400 mg of the above title compound.

g) N-[2-(R)-amino-3-mercaptopropyl]-L-penicillaminyl-1,2,3,4-tetrahydro-3(S)-isoquinoline carbonyl methionine methylester cyclic disulfide Crude N-[2(R)-(t-butoxycarbonyl)amino-3-mercaptopropyl]-L-penicillaminyl]-1,2,3,4-tetrahydro-3(S)-isoquinoline carbonyl methionine methylester cyclic disulfide (400 mg) was treated with 90% trifluoroacetic acid (TFA) in water TFA/$H_2O$ (9:1)(10 ml) for 30 min. Volatile substances were removed in vacuo to dryness, and a trace of TFA was evaporated with toluene several times and triturated with hexane, decanted, and then dried. Crude product was subjected to preparative high performance liquid chromatography (HPLC) using $C_{18}$ column and 0.1% TFA and $CH_3CN$ as mobile phase. Appropriate fractions were pooled, and solvents were removed giving the above title compound as a white solid (78 mg). M/e=541.1.

EXAMPLE 2

N-[2-(R)-amino-3-mercaptopropyl]-L-[8-acetamidomethyl-penicillaminyl]-1,2,3,4-tetrahydro-3(S)-isoquinoline carbonyl methionine (Compound 4)

To a solution of N-[2(R)-(t-butoxycarbonyl)-amino-3-triphenylmethylmercaptopropyl]-L-[s-acetamidomethyl penicillaminyl]-1,2,3,4-tetrahydro-3(S)-isoquinolinecarbonyl methionine methylester (Example 1 e))(500 mg) in 10 MeOH (50 ml) was added 2 ml 2 N—NaOH. After 30 min., most of MeOH was removed in vacuo to a small volume, diluted with water, acidified with 5% aqueous citric acid, and extracted with ethylacetate. The ethylacetate extract was then dried ($MgSO_4$). Solvent was evaporated in vacuo to dryness. The residue was treated with 50% TFA in $CH_2Cl_2$ containing triethylsilane ($Et_3SiH$) (0.5 ml) for 40 min. Volatile substances were removed in dryness, and a trace of TFA was evaporated with toluene and then dried. Crude product was purified by prep. HPLC giving the above titled compound (100 mg) as a white solid. M/e=600.2

EXAMPLE 3

N-[2-(R)-amino-3-mercaptopropyl]-L-penicillaminyl]-2,3-dimethylanilide cyclic disulfide (Compound 9)

a) [N-t-Butoxycarbonyl-S-acetamidomethyl]penicillaminyl-2,3-dimethylanilide

To an ice-cooled solution of N-[t-butoxycarbonyl]-S-acetamidomethyl penicillamine (Bachem California, Torrance, Calif.) (0.64 g), 2,3-dimethylaniline (0.25 g), hydroxybenzotriazole (0.41 g) in dimethylformide (DMF)/$CH_2Cl_2$ (1:1, 20 ml) was added 1-(3-dimethylaminopropyl) -3-ethylcarbodiimide (EDC) (0.57 g). The mixture was stirred at 0–52C for 30 min. and then the temperature was slowly allowed to room temperature overnight. After evaporation of the solvents, the residue was partitioned between ethyl acetate (EtOAc) and water. EtOAc extract was washed with aqueous $NaHCO_3$, water, and then dried ($MgSO_4$). The solvent was evaporated in vacuo to dryness. The residue was chromatographed on silica gel (40 g) using $CHCl_3$/acetone= 19:1 as eluants, appropriate fractions were pooled, and solvents were removed in vacuo to dryness giving 350 mg of the above titled compound. TLC (silica gel: $CHCl_3$/ acetone=4:1, Rf–0.77).

b) L-[S-acetamidomethylpenicillaminyl-2,3-dimethyl anilide TFA salt

[N-t-butoxycarbonyl-S-acetamidomethyl]-penicillaminyl-2,3-dimethylanilide was treated with 50% TFA in $CH_2Cl_2$ (20 ml) for 30 min. Volatile substances were removed in vacuo to dryness. Trace of TFA was removed by co-evaporation with toluene several times. The TFA salt was dissolved in $CHCl_3$ (30 ml), treated with excess triethylamine, washed with water, dried ($MgSo_4$), and solvent was evaporated in vacuo to give free base.

c) N-[2(R)-(t-butoxycarbonyl)amino-3-triphenylmethylmercapto propyl]-L-[S-acetamidomethylpenicillaminyl-2,3-dimethylamilide To a stirred solution of 2(R)-t-butoxycarbonylamino-3-triphenylmethylmercaptopropanal (0.5 g; Example 1b) and L-[S-acetamidomethylpenicillaminyl-2,3-dimethylanilide TFA salt (0.3 g) in MeOH containing 1% acetic acid (HOAc) (10 ml) was added portionwise $NaCNBH_3$ (100 mg). The mixture was stirred at room temperature overnight. Most of the solvent was evaporated in vacuo to a small volume, which was partitioned between EtOAc and water. EtOAc layer was further washed with aqueous $NaHCO_3$, water, and then dried ($MgSO_4$). After evaporation of solvent, the residue was chromatographed on silica gel (30 g) using $CHCl_3$-acetone (19:1 to 9:1) as eluants. Appropriate fractions were pooled, and solvents were evaporated in vacuo to dryness giving 360 mg of the above titled compound. TLC (silica gel: $CHCl_3$/acetone=9:1, Rf=0.13.

d) N-[2-(R)-amino-3-mercaptopropyl]-L-penicillaminyl]-2,3-dimethylamilide cyclic disulfide To a stirred solution of N-[2(R)-(t-butoxycarbonyl) amino-3-triphenylmethylmercaptopropyl]-L-[S-acetamidomethyl penicillaminyl]-2,3-dimethylamilide (350 mg) in 50 ml 90% MeOH in water was added a solution of iodine (250 mg) in MeOH (5 ml). After 1 hour, most of the solvent was evaporated in vacuo to a small volume, diluted with water, extracted with EtOAc. EtOAc layer was washed with aqueous $Na_2S_2O_3$, water, then dried ($MgSO_4$). Solvent was removed in vacuo to dryness (220 mg), treated with 90% aqueous TFA (ml) for 30 min, and volatile substances were removed in vacuo to dryness. Crude product was purified by preparative HPLC giving 62 mg of the above titled compound as a white solid. M/e=340.2.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A compound of the formula I or formula II

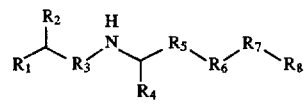

Formula I

-continued

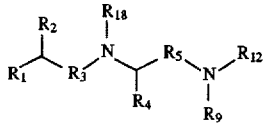

Formula II wherein $R_1$ is $N(R_{10})(R_{11})$;

$R_2$ is thio lower alkyl;

each of $R_3$ and $R_5$, independently, is $CH_2$ or $C(O)$;

$R_4$ is thio lower alkyl, wherein the free thio groups of $R_2$ and $R_4$ form a disulfide bond;

$R_6$ is a residue of a natural or synthetic α-amino acid $R_7$ is a residue of a natural or synthetic α-amino acid;

$R_8$ is OH or lower alkoxy, or, together with $R_7$, forms homoserinelactone;

each of $R_9$, $R_{10}$, $R_{11}$, independently, is H or lower alkyl;

$R_{12}$ is a substituted or unsubstituted moiety selected from cycloalkyl, cycloalkyl lower alkyl, aryl, aryl lower alkyl, heterocycle, and heterocycle lower alkyl, wherein the substituent is lower alkyl, aryl, halo, lower alkoxy, or $C(O)-R_7-R_8$;

$R_{13}$ is lower alkyl, aryl, or aryl lower alkyl;

$R_{18}$ is H or, together with $R_9$, forms $-CH_2CH_2-$;

or a pharmaceutically acceptable salt thereof.

2. A compound of claim 1, wherein said compound is of formula I; or a pharmaceutically acceptable salt thereof.

3. A compound of claim 1, wherein said compound is of formula II; or a pharmaceutically acceptable salt thereof.

4. A compound of claim 2, wherein $R_6$ is $-N(R_{14})CH(R_{15})C(O)-$ where $R_{14}$ is H or lower alkyl, and $R_{15}$ is a substituted or unsubstituted moiety selected from lower alkyl, aryl, aryl lower alkyl, heterocycle, and heterocycle lower alkyl, in which said substituent is lower alkyl, halo, or lower alkoxy, or $R_{15}$, together with $N(R_{14})C$ attached thereto, form a heterocycle;

$R_7$ is $-N(R_{16})CH(R_{17})C(O)-$ where $R_{16}$ is H or lower alkyl; and $R_{17}$ is $(CH_2)_mS(O)_nCH_3$ where m is 1-6 and n is 0-2, or is a substituted or unsubstituted moiety selected from lower alkyl and thio lower alkyl, where said substituent is $C(O)N(R_{10})(R_{11})$; and $R_8$ is OH or lower alkoxy;

or a pharmaceutically acceptable salt thereof.

5. A compound of claim 4, wherein $R_2$ is $CH_2SH$; and $R_4$ is $C(CH_3)_2SH$ or $CH_2SH$;

in which the free thio groups of $R_2$ and $R_4$ form a disulfide bond; or a pharmaceutically acceptable salt thereof.

6. A compound of claim 5, wherein $R_{15}$, together with $N(R_{14})C$ attached hereto, form a heterocycle; $R_{16}$ is H; and $R_{17}$ is $(CH_2)_2S(O)_nCH_3$; or a pharmaceutically acceptable salt thereof.

7. A compound of claim 6, wherein $R_1$ is $NH_2$;

$R_3$ is $CH_2$;

$R_5$ is $C(O)$; and $R_8$ is OH or $OCH_3$;

or a pharmaceutically acceptable salt thereof.

8. A compound of claim 3, wherein $R_2$ is $CH_2SH$; and $R_4$ is $C(CH_3)_2SH$ or $CH_2SH$;

in which the free thio groups of $R_2$ and $R_4$ form a disulfide bond; or a pharmaceutically acceptable salt thereof.

9. A compound of claim 8, wherein $R_{12}$ is substituted or unsubstituted aryl, or substituted or unsubstituted aryl lower alkyl, and $R_{18}$ is H; or a pharmaceutically acceptable salt thereof.

10. A compound of claim 9, wherein $R_1$ is $NH_2$;

$R_3$ is $CH_2$;

$R_5$ is $C(O)$;

$R_9$ is H; and $R_{12}$ is substituted or unsubstituted phenyl or benzyl, where said substituent is lower alkyl or halo; or a pharmaceutically acceptable salt thereof.

11. A compound of claim 1, said compound of the formula

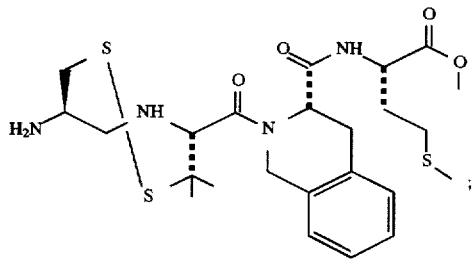

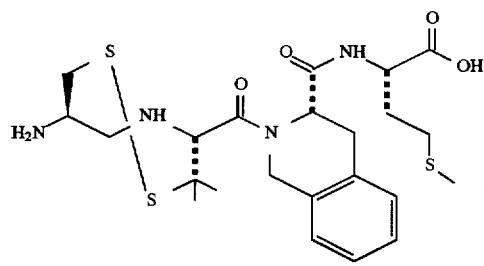

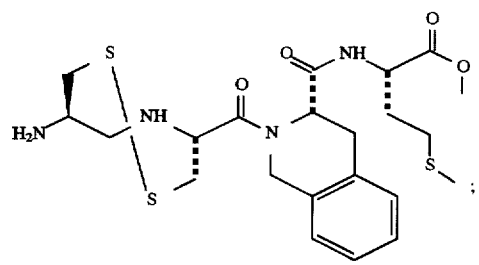

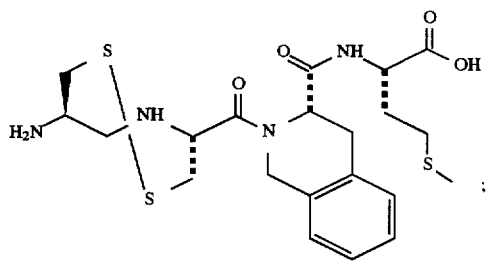

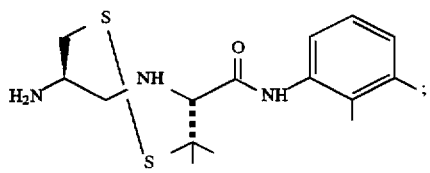

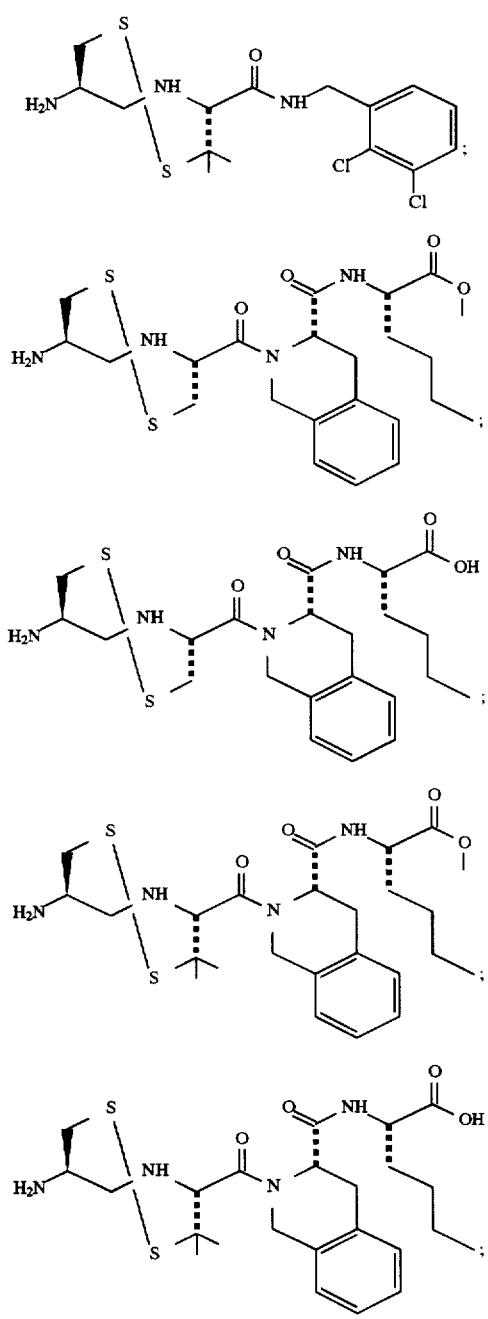

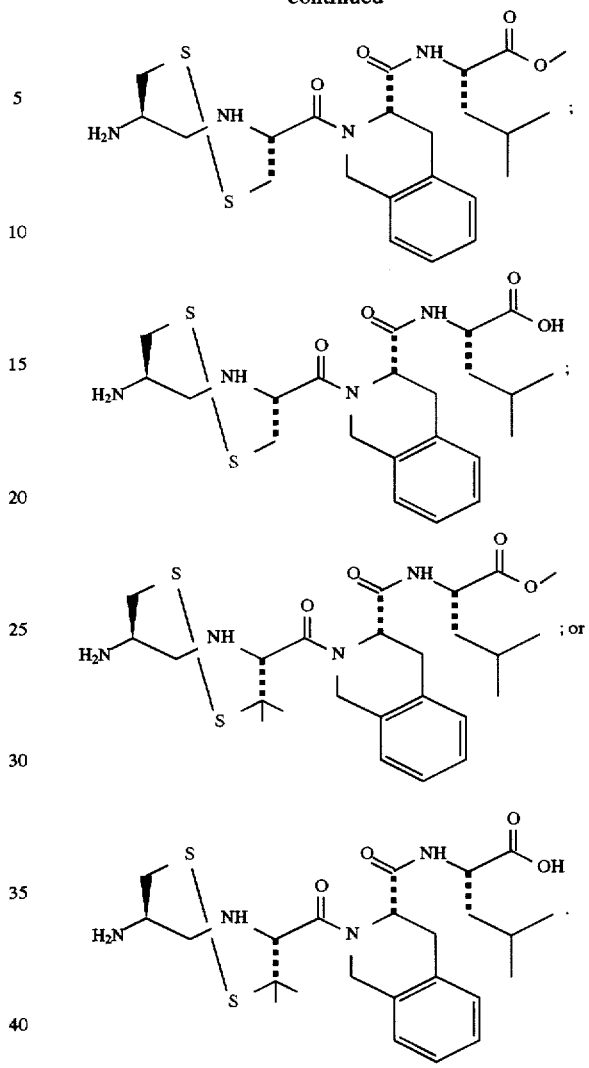

12. A method of treating tumors or restenosis in a subject in need of said treatment, which comprises administering to said subject a therapeutically effective amount of the compound or salt of claim 1.

13. A method of treating tumors or restenosis in a subject in need of said treatment, which comprises administering to said subject a therapeutically effective amount of a compound or salt thereof according to claim 11.

14. A pharmaceutical composition comprising a compound of claim 1 and a pharmaceutically-acceptable carrier.

* * * * *